United States Patent [19]

Messmer et al.

[11] Patent Number: 4,753,938

[45] Date of Patent: * Jun. 28, 1988

[54] CONDENSED AS-TRIAZINE DERIVATIVES

[75] Inventors: Andras Messmer; Sandor Batori; Gyorgy Hajos; Pal Benko; Laszlo Pallos; Lujza Petocz; Katalin Grasser; Eniko Szirt nee Kiszelly, all of Budapest, Hungary

[73] Assignee: Richter Gedeon Vegyeszeti Gyar Rt., Budapest, Hungary

[ * ] Notice: The portion of the term of this patent subsequent to Jul. 22, 2003 has been disclaimed.

[21] Appl. No.: 787,704

[22] Filed: Oct. 15, 1985

Related U.S. Application Data

[63] Continuation of Ser. No. 652,600, Sep. 20, 1984, abandoned.

[30] Foreign Application Priority Data

Sep. 20, 1983 [HU] Hungary .................. 3243/83

[51] Int. Cl.⁴ .................. C07D 253/08; A61K 31/53
[52] U.S. Cl. .................. 514/243; 544/183
[58] Field of Search .................. 544/183; 514/243

[56] References Cited

U.S. PATENT DOCUMENTS 4,419,355 12/1983 Kosoczky et al. .................. 544/183
4,602,018 7/1986 Messmer et al. .................. 544/183

Primary Examiner—John M. Ford
Attorney, Agent, or Firm—Keil & Weinkauf

[57] ABSTRACT

The invention relates to new compounds of the general Formula I

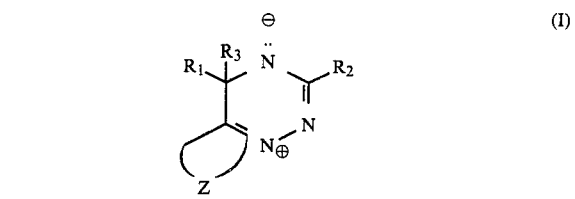

and isomers thereof wherein $R_1$ is $C_{1-10}$ alkyl, $C_{3-6}$ cycloalkyl or phenyl, naphthyl or phenyl-($C_{1-4}$ alkyl), wherein the aryl ring of the three latter groups may optionally bear one or more halogen, nitro, trifluoromethyl, amino, hydroxy, $C_{1-4}$ alkyl and/or $C_{1-4}$ alkoxy substituent(s);

$R_2$ stands for hydrogen, halogen, hydroxy, oxo, $C_{1-4}$ alkyl, $C_{1-4}$ alkoxy, phenyl or naphthyl, wherein the two latter groups may optionally bear one or more halogen, nitro, trifluoromethyl, amino, hydroxy, $C_{1-4}$ alkyl and/or $C_{1-4}$ alkoxy substituent(s);

$R_3$ represents hydrogen, hydroxy or $C_{1-4}$ alkoxy;

Z is buta-1,3-dienyl or a group of the general Formula (a)

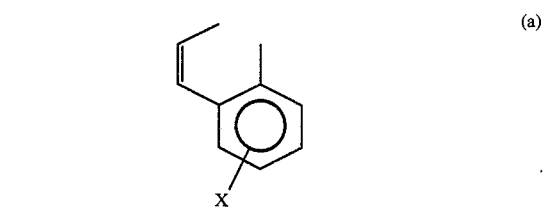

or (b)

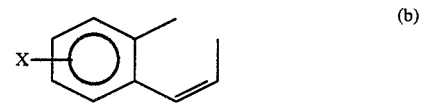

and
X is hydrogen or halogen.

The compounds of the general Formula I possess useful pharmacological properties, particularly antidepressant and antiarrhythmial effect.

9 Claims, No Drawings

CONDENSED AS-TRIAZINE DERIVATIVES

This application is a continuation of application Ser. No. 652,600, filed on Sept. 20, 1984, now abandoned.

This invention relates to new "Zwitterion" type condensed as-triazine derivatives, a process for the preparation thereof and pharmaceutical compositions containing the same.

According to an aspect of the present invention there are provided new compounds of the general Formula I

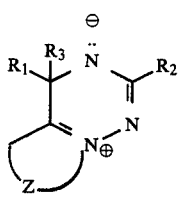

and isomers thereof wherein
$R_1$ is $C_{1-10}$ alkyl, $C_{3-6}$ cycloalkyl or phenyl, naphthyl or phenyl-($C_{1-4}$ alkyl), whereby the aryl ring of the three latter groups may optionally bear one or more halogen, nitro, trifluoromethyl, amino, hydroxy, $C_{1-4}$ alkyl and/or $C_{1-4}$ alkoxy substituent(s);
$R_2$ stands for hydrogen, halogen, hydroxy, oxo, $C_{1-4}$ alkyl, $C_{1-4}$ alkoxy, phenyl or naphthyl, whereby the two latter groups may optionally bear one or more halogen, nitro, trifluoromethyl, amino, hydroxy, $C_{1-4}$ alkyl and/or $C_{1-4}$ alkoxy substituent(s);
$R_3$ represents hydrogen, hydroxy or $C_{1-4}$ alkoxy;
Z is buta-1,3-dienyl or a group of the general Formula (a)

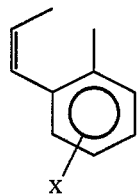

or (b)

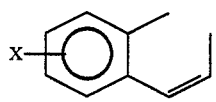

and
X is hydrogen or halogen.

The term "alkyl" used throughout the specification relates to straight or branched chained alkyl groups (e.g. methyl, ethyl, n-propyl, isopropyl, tert. butyl etc.). The term "alkoxy" relates to straight or branched chained alkoxy groups (e.g. methoxy, ethoxy, isopropoxy etc.). The term "halogen" encompasses the fluorine, chlorine, bromine and iodine atoms.

$A^-$ as used throughout the specification stands for a suitable inorganic or organic anion, e.g. chloride, bromide, iodide, perchlorate, methane sulfonate, ethane sulfonate or p-toluene sulfonate etc.

Then "$C_{3-6}$ cycloalkyl group" may be a cyclopropyl, cyclobutyl, cyclopentyl or cyclohexyl group. The phenyl-($C_{1-4}$ alkyl)-group may be benzyl, phenylethyl etc.

According to a preferred feature of the present invention there are provided compounds of the general Formula I, wherein Z is a group of the Formula (b) and X represents hydrogen. According to a further preferred feature of the present invention there are provided compounds of the general Formula I, wherein $R_1$ stands for phenyl optionally substituted by halogen in position 4, particularly for 4-chloro-phenyl. $R_3$ is advantageously hydroxy or methoxy.

Particularly preferred representatives of the compounds of the general Formula I are the following derivatives:
1-(4-chloro-phenyl)-1-hydroxy-as-triazino[6,1-a]isoquinoline-5-ium-2-(1H)-ide;
1-(4-chloro-phenyl)-as-triazino[6,1-a]isoquinoline-5-ium-2-(3H)-ide-3-one;
1-(4-chloro-phenyl)-1-methoxy-as-triazino[6,1-a]isoquinoline-5-ium-2-(1H)-ide.

According to a further aspect of the present invention there is provided a process for the preparation of compounds of the general Formula I and isomers thereof which comprises
(a) reacting a compound of the general Formula II

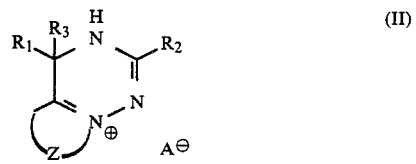

(wherein $R_1$, $R_2$, $R_3$, X and Z are as stated above and $A^-$ represents an anion) with a base; or
(b) for the preparation of compounds of the general Formula I, wherein $R_3$ is $C_{1-4}$ alkoxy, reacting a compound of the general Formula III

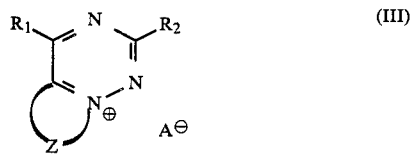

(wherein $R_1$, $R_2$, $A^-$, Z and X are as stated above) with a $C_{1-4}$ metal alcoholate; or
(c) for the preparation of compounds of the general Formula I, wherein $R_3$ is hydroxy, reacting a compound of the general Formula III with the aqueous solution of a base; or
(d) reacting a compound of the general Formula IV

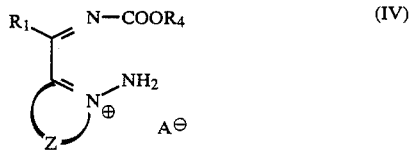

(wherein $R_1$, Z and $A^-$ are as stated above) with an alkali metal or alkaline earth metal base in aqueous medium; or
(e) for the preparation of compounds of the general Formula I, wherein $R_3$ is hydrogen, reducing a compound of the general Formula III and treating the dihydro compound thus obtained—if desired, without isolation—with a base; or (f) for the preparation of compounds of the general Formula I, wherein $R_3$ is $C_{1-4}$ alkoxy, alkylating the corresponding compound of the general Formula I, wherein $R_3$ is hydroxy; or (g) for the preparation of compounds of the general Formula I, wherein $R_2$ is halogen, reacting a compound of the general Formula IV with an alkali metal or alkaline earth metal base, and treating the product formed with a halogenating agent;

and, if desired, separating a compound of the general Formula I thus obtained into the isomers thereof.

According to method (a) of the process of the present invention a compound of the general Formula II is reacted with a base. In the starting materials of the general Formula II $A^-$ may stand for any suitable inorganic or organic anion, e.g. a halide (such as chloride, bromide or iodide), perchlorate, methane sulfonate, ethane sulfonate or p-toluene sulfonate anion etc. As base any organic base or alkali metal or alkaline earth metal base may be applied, preferably a carbonate, hydrogen carbonate, hydroxide or alcoholate of an alkali metal or alkaline earth metal. As reaction medium such solvents can be used in which the base and the starting material are sufficiently soluble. As such solvent preferably an alkanol (e.g. methanol or ethanol), ester (e.g. ethyl acetate), ether (e.g. dioxane, tetrahydrofuran or diethyl ether) or ketone (e.g. acetone) may be used. The reaction may be accomplished at a temperature between 20 C.° and 100 C.°, preferably at room temperature.

According to method (b) of the process of the present invention compounds of the general Formula I, wherein $R_3$ is $C_{1-4}$ alkoxy, are prepared by reacting a compound of the general Formula III with a $C_{1-4}$ metal alcoholate. As reactant preferably an alkali or alkaline earth metal alcoholate may be used (e.g. sodium or potassium alcoholate). The reaction may be carried out in a solvent which forms an anion with the desired alcoholate. It is preferred to use as reaction medium the alkanol which corresponds to the alcoholate. One may also proceed by using a solid alcoholate and applying as reaction medium an anhydrous solvent which is capable of dissolving the said alcoholate (e.g. an ether, such as tetrahydrofurane, dioxane or diethyl ether; or an aromatic hydrocarbon, e.g. benzene or toluene). The alcoholate may be used in equimolar amount or in a small excess. The reaction may be accomplished at 0–100 C.°, preferably at room temperature.

According to method (c) of the process of the present invention compounds of the general Formula I, wherein $R_3$ is hydroxy, are prepared by reacting a compound of the general Formula III with the aqueous solution of an inorganic base. For this purpose an alkali or alkaline earth metal carbonate or hydroxide may be used. The reaction may be carried out in aqueous medium or in an organic solvent partially miscible with water (e.g. an alkanol, aromatic hydrocarbon, ether or ester). The reaction may be preferably accomplished at ambient temperature.

According to method (d) of the process of the present invention a compound of the general Formula IV is reacted with an alkali metal or alkaline earth metal base. Thus compounds of the general Formula I containing various $R_3$ groups may be obtained, depending on the nature and character of the base used. $R_4$ is preferably alkoxy.

If strong bases are used (e.g. an alkali hydroxide), compounds of the general Formula I are obtained in which $R_3$ represents hydroxy. If an alkali metal alcoholate (e.g. sodium methylate, potassium ethylate, potassium tertiary butylate) is used as base, compounds of the general Formula I are obtained in which $R_3$ is alkoxy. If weak bases are used (e.g. sodium carbonate, potassium carbonate, sodium hydrogen carbonate or potassium hydrogen carbonate), compounds of the general Formula I are obtained in which $R_3$ is hydrogen.

According to method (e) of the process of the present invention compounds of the general Formula I, wherein $R_3$ is hydrogen, are prepared by reducing a compound of the general Formula III and treating the product thus obtained—after or without isolation—with a base. Reduction may be preferably accomplished by means of catalytic hydrogenation. As catalyst e.g. palladium, platinum oxide or ruthenium oxide may be used; the catalyst may be optionally used on a carrier. Catalytic hydrogenation may be preferably carried out in a buffered system. It is preferred to use a mixture of sodium acetate and acetic acid for this purpose. Hydrogenation may be carried out at ambient temperature or at elevated temperature and at atmospheric pressure or under higher pressure. The product obtained is treated with a base after or without isolation. As base e.g. a hydroxide, carbonate, hydrogen carbonate or alcoholate of an alkali or alkaline earth metal may be used.

According to method (f) of the process of the present invention a compound of the general Formula I, wherein $R_3$ is hydroxy, is alkylated to yield the corresponding compound of the general Formula I, wherein $R_3$ is alkoxy. Alkylation may be carried out by methods known per se. As alkylating agent e.g. an alkyl halide or dialkyl sulfate may be used. Alkylation may be preferably accomplished in the presence of a base (e.g. an alkali metal hydroxide or alcoholate). The alkylating agent may be used in equimolar amount or in a small excess. The reaction may be carried out at a temperature between 0 C.° and room temperature.

According to method (g) of the process of the present invention compounds of the general Formula I, wherein $R_2$ is halogen, are prepared by reacting a compound of the general Formula IV with an alkali metal or alkaline earth metal base. As base preferably alkali hydroxides, alkali alcoholates, alkali carbonates or alkaline earth metal hydroxides are used. The product is reacted with a halogenating agent, preferably phosphorous oxychloride or phosphorous trichloride.

The compound of the general Formula I thus obtained may be separated into the isomers by methods known per se, if desired.

The starting materials of the general Formula II are new compounds which are disclosed and claimed in the Hungarian patent application Ser. No. 3242/83.

The starting materials of the general Formula II, wherein $R_3$ is hydroxy, may be prepared by reacting a compound of the general Formula III with water. Starting materials of the general Formula II, wherein $R_3$ is $C_{1-4}$ alkoxy, can be prepared by reacting a compound of the general Formula III with a $C_{1-4}$ metal alcoholate.

The starting materials of the general Formulae III and IV are known compounds (DOS No. 3,128,386).

According to a further aspect of the present invention there are provided pharmaceutical compositions comprising as active ingredient at least one compound of the general Formula I or an isomer thereof in admixture with suitable inert solid or liquid pharmaceutical carriers. The said pharmaceutical compositions may be prepared by methods of pharmaceutical industry known per se. The compositions may be finished in solid (e.g. tablets, pills, coated pills, dragées, capsules), semi-solid (e.g. ointments) or liquid (e.g. solutions, suspensions or emulsions) form. The compositions may be suitable for oral or parenteral administration.

The compositions of the present invention may contain carriers, e.g. solid carriers, fillers, sterile aqueous solutions or non-toxic organic solvents. The tablets suitable for oral administration may contain sweetening agents and/or other auxiliary agents (e.g. starch, particularly potato starch). The said compositions may also contain binding agents (e.g. polyvinyl pyrrolidone), sliding agents (e.g. magnesium stearate, sodium lauryl sulfate or talc), or other additives (e.g. sodium citrate, calcium carbonate, dicalcium phosphate etc.). The aqueous suspensions or elixirs suitable for oral administration may also comprise flavourants, dyestuffs, emulsifiers or diluents (e.g. water, ethanol, propylene glycol or glycerol etc.).

The pharmaceutical compositions for parenteral administration may comprise pharmaceutically acceptable solvents (e.g. sesame oil, peanut oil, aqueous propylene glycol, dimethyl formamide etc.) or—when water-soluble active ingredients are used—water. The aqueous solutions may be adjusted to the desired pH-value by means of a buffer or to the isotonic value by using suitable liquid diluents (e.g. sodium chloride or glucose). The aqueous solutions are suitable first of all for intravenous, intramuscular or intraperitoneal administration. The sterile aqueous solutions may be prepared by methods known per se.

The daily dosage of the compounds of the general Formula I may vary between wide ranges and depends on various factors (e.g. the efficiency of the active ingredient, the method of administration, the state and condition of the patient etc.).

The pharmacological activity of the compounds of the general Formula I is shown by the following tests.

(1) Acute toxicity on mice

The test is carried out on male and female white mice belonging to the CFLP strain and weighing 18–22 g. The test compound is administered orally and the animals are observed for a period of 7 days. In the groups for each dose half of the animals are male and the other half are female. The animals are kept in a plastic box (39×12×12 cm) on scrapings litter at room temperature. The mice receive standard fodder and tap water ad libitum. The toxicity data are determined by the method of Litchfield-Wilcoxon.

The test compounds are used in a suspension formed with 0.5% carboxymethyl cellulose.

The results are summarized in Table I.

TABLE I

| Test compound | Toxicity on mice LD$_{50}$ mg./kg. p.o. |
| --- | --- |
| Compound A | 550 |
| Compound B | 420 |
| Compound C | 2000 |
| Amitriptyline | 225 |
| Reference Compound D | 600 |

(2) Antagonism of Tetrabenazine ptosis on mice and rats, p.o.

Groups of 10 mice each are treated orally with the test compound whereupon after 30 minutes 50 mg./kg. of Tetrabenazine are administered intraperitoneally and the animals showing ptosis (eyelid-closure) are counted in each group after 30, 60, 90 and 120 minutes, respectively.

The results are evaluated as follows: on the basis of all the measured data an average ptosis is calculated for each group and the deviation from the average of the control group is expressed in percents (inhibition). The ED$_{50}$ values are calculated from the data thus obtained.

The results obtained are summarized in Table II.

TABLE II

| Antagonism of tetrabenazine ptosis on mice and rats | | | |
| --- | --- | --- | --- |
| | Mice | | Rats |
| Test compound | ED$_{50}$ mg./kg. | Ther. index | ED$_{50}$ mg./kg. |
| Compound A | 0.15 | 3667 | 7 |
| Compound B | 0.25 | 1680 | 0.6 |
| Compound C | 23.00 | 87 | |
| Reference compound D | 3.2 | 188 | 5.6 |
| Amitriptyline | 12.00 | 19 | 11.50 |

(3) Antagonism of reserpine ptosis on mice, p.o.

Animal groups consisting of 10 mice each are treated subcutaneously with 6 mg./kg. of reserpine. The test compound is administered orally after 60 minutes. The animals showing a ptosis are counted after 60 and 120 minutes. The evaluation is carried out as described in connection with the previous ptosis test No. 2. The results are summarized in the following Table III.

TABLE III

| Antagonism of reserpine ptosis on mice | | |
| --- | --- | --- |
| Test compound | ED$_{50}$ mg./kg. | Ther. index |
| Compound A | 28.0 | 19.6 |
| Compound B | 1.5 | 280.0 |
| Reference compound D | above 120 | below 5.0 |
| Amitriptyline | 65.0 | 3.45 |

(4) Antagonism of reserpine ptosis on rats, p.o.

Animal groups consisting of 10 rats each are treated subcutaneously with 2.5 mg./kg. of reserpine whereupon after 60 minutes the test compound is administered orally. The animals showing ptosis are counted until the effect decreases. The evaluation is carried out as described in connection with the previous ptosis test (test 2).

The results are summarized in the following Table IV.

TABLE IV

| Antagonism of reserpin ptosis on rats | |
| --- | --- |
| Test compound | ED$_{50}$ mg./kg. |
| Compound A | 28 |
| Compound B | 34 |
| Reference compound D | 60 |
| Amitriptyline | about 140 |

(5) Potentiation of yohimbine toxicity on mice

The tests are carried out according to the method of Quinton. Animal groups consisting of 10 mice each are treated with the test compound. After an hour a sublethal dose of yohimbine is administered intraperitoneally at a rate of 20 ml./kg. The killed animals are counted after 1 and 24 hours, respectively. The results are summarized in Table V.

TABLE V

| | Potentiation of yohimoine toxicity | |
|---|---|---|
| Test compound | ED$_{50}$ mg./kg. | Ther. index |
| Compound A | 5.0 | 110 |
| Compound B | 1.2 | 350 |
| Amitriptyline | 12.5 | 18 |

(6) Antiarrhythmial effect on rats

The test is carried out according to the modified method of Marmo et al. The test animals are narcotized with ethyl urethane (1.2 g./kg. i.p.). Aconitine is administered intravenously in the form of a bolus injection in a dose of 75 μg./kg. The changes of ECG are followed in standard II outlet 5 minutes after the administration of aconitine. The changes observed are evaluated with the aid of a scale from 0 to 5 points. The test compound is administered either intravenously 2 minutes before the addition of aconitine, or orally 1 hour before the aconitine administration.

The results are summarized in Table VI.

TABLE VI

| Test compound | Dose | Inhibition, % |
|---|---|---|
| Compound A | 1 mg./kg. | 39.6 |
| Compound B | 1 mg./kg. | 44.3 |
| Lidocain | 4 mg./kg. | 23.4 |

(7) Antitremorine effect on mice 20 mg./kg. of tremorine are administered i.p. to mice whereupon after 45 minutes the induced characteristic tremor is registered. The test compounds are administered orally 1 hour before the addition of tremorine. The results are summarized in Table VII.

TABLE VII

| | Antitremorine effect on mice | |
|---|---|---|
| Test compound | ED$_{50}$ mg./kg. | Ther. index |
| Compound B | 40 | 10.5 |
| Reference compound D | inactive | — |

The following test compounds are used:

Compound A=1-(4-chloro-phenyl)-1-hydroxy-as-triazino[6,1-a]isoquinoline-5-ium-2-(1H)-ide (Example 2)

Compound B=1-(4-chloro-phenyl)-1-methoxy-as-triazino[6,1-a]isoquinoline-5-ium-2-(1H)-ide (Ex. 10)

Compound C=1-(4-chloro-phenyl)-as-triazino[6,1-a]isoquinoline-5-ium-2-(1H)-ide-3-one (Ex. 9.)

Reference compound D=1-(4-chloro-phenyl)-as-triazino[6,1-a]isochinolinium-bromide (Example 5 of DOS No. 3,128,386)

Amitriptyline=N,N-dimethyl-3-[dibenzo[a,d]-cycloheptadiene-5-ylidene]propylamine Lidocain=α-diethylamino-2,6-dimethyl-acetanilide.

Summarized it can be stated that the new compounds of the present invention possess outstanding antidepressant and antiarrhythmial effects. The activity of the compounds of the general Formula I is by orders of magnitude higher than that of the most active compound disclosed in DOS No. 3,128,386 both in respect of the absolute dose and the therapeutical index on the tetrabenazine antagonism test on mice and rats.

On the reserpine ptosis test the activity of the compounds of the present invention is significantly higher than that of the reference compound D. In addition to this surprising and unforseen increase of effect, the activity spectrum of the compounds of the general Formula I differs also qualitatively from that of the compounds disclosed in DOS No. 3,128,386 which manifests itself in the appearence of therapeutically highly favourable tranquillant, analgesic, local anaesthetic and antitremorine effects.

The daily dosage of the compounds of the general Formula I may vary between wide ranges and depends on various factors of the given case, as already mentioned above. As a matter of information it may be noted that the average oral daily dosage of the compounds of the general Formula I is about 5–150 mg. which may be augmented up to 300 mg. in serious cases. The daily parenteral dose may amount approximately to 5–50 mg.

Further details of the present invention are to be found in the following Examples without limiting the scope of protection to the said Examples.

EXAMPLE 1

Preparation of 1-(4-chloro-phenyl)-1-ethoxy-3-chloro-as-triazino[6,1-a]isoquinolin-5-ium-2-(1H)-ide To a solution of 5 g (0.012 mole) of 1-(4-chlorophenyl)-3-chloro-as-triazino[6,1-a]isoquinolinium-perchlorate and 50 ml of ethanol a sodium ethylate solution containing 0.012 mole of sodium is added under cooling. 3.2 g of the aimed compound precipitate in the form of yellow crystals, yield 72%, mp.: 283–284 C.°.

EXAMPLE 2

Preparation of 1-(4-chloro-phenyl)-1-hydroxy-as-triazino[6,1-a]isoquinolin-5-ium-2-(1H)-ide To a solution of 4.1 g (0.01 mole) of 1-(4-chlorophenyl)-1-hydroxy-1,2-dihydro-as-triazino[6,1-a]isoquinolinium-perchlorate in ethanol 11 ml of a sodium hydroxide solution (1 mole/l) are added and the product is precipitated by adding water. Thus 2.5 g of the desired compound are obtained, yield 81%, mp.: 143–145 C.°.

Preparation of 1-phenyl-1-hydroxy-as-triazino[6,1-a]isoquinolin-5-ium-2-(1H)-ide One proceeds according to Example 2 except that 1-phenyl-1-hydroxy-1,2-dihydro-as-triazino[6,1-a]isoquinolinium-perchlorate is used as starting material. The aimed compound is obtained in a yield of 78%, mp: 146–147 C.°.

EXAMPLE 4

Preparation of 1-(4-fluoro-phenyl)-1-hydroxy-as-triazino[6,1-a]isoquinolin-5-ium-2-(1H)-ide One proceeds according to Example 2 except that 1-(4-fluoro-phenyl)-1-hydroxy-1,2-dihydro-as-triazino[6,1-a]isoquinolinium-ethanesulfonate is used as starting material. The aimed compound is obtained in a yield of 72%, mp.: 113–114 C.°.

EXAMPLE 5

Preparation of 1-(3-trifluoromethyl-phenyl)-1-hydroxy-as-triazino[6,1-a]isoquinolin-5-ium-2-(1H)-ide One proceeds according to Example 2 except that 1-(3-trifluoromethyl-phenyl)-1-hydroxy-1,2-dihydro-astriazino[6,1-a]isoquinolinium-bromide is used as starting material. The desired compound is obtained in a yield of 68%, mp.: 158–159 C.°.

EXAMPLE 6

Preparation of 1-(4-fluoro-phenyl)-1-hydroxy-10-chloro-as-triazino[6,1-a]isoquinolin-5-ium-2-(1H)-ide One proceeds according to Example 2 except that 1-(4-fluoro-phenyl)-1-hydroxy-1,2-dihydro-10-chloro-as-triazino[6,1-a]isoquinolinium-chloride is used as starting material. The desired compound is obtained with a yield of 65%, mp.: 150–151 C.°.

EXAMPLE 7

Preparation of 4-phenyl-4-hydroxy-as-triazino[1,6-a]quinolin-11-ium-3-(4H)-ide

To a solution of 3.6 g (0.01 mole) of 4-phenyl-as-triazino[1,6-a]quinolinium-perchlorate in ethanol 11 ml of a 4% aqueous sodium hydroxide solution are added. 2.5 g of the aimed compound precipitate, yield 91%, mp.: 137–138 C.°.

Preparation of 1,3-diphenyl-1-hydroxy-pyrido[1,2-f]-as-triazin-5-ium-2-(1H)-ide

One proceeds according to Example 7 except that 1,3-diphenyl-pyrido[2,1-f]-as-triazinium-perchlorate is used as starting material and acetonitrile is used as reaction medium, instead of ethanol. The aimed compound is obtained with a yield of 93%, mp.: 168–169 C.°.

EXAMPLE 9

Preparation of 1-(4-chloro-phenyl)-as-triazino[6,1-a]isoquinolin-5-ium-2-(3H)-id-3-one To a solution of 1 g (0.0022 mole) of N-amino-1-isoquinolyl-(4-chloro-phenyl)-N'-ethoxycarbonyl-ketimine-perchlorate in acetonitrile 2 ml of a 10% aqueous sodium carbonate solution are added. The product precipitates after a short time. Thus 0.5 g of the desired compound is obtained, yield 74%, mp.: 310 C.°/decomposition/.

EXAMPLE 10

Preparation of 1-(4-chloro-phenyl)-1-methoxy-as-triazino[6,1-a]isoquinolin-5-ium-2-(1H)-ide 1-(4-chloro-phenyl)-as-triazino[6,1-a]isoquinolinium-perchlorate is reacted with methanol in an analogous manner to that described in Example 1. The aimed compound is obtained with a yield of 83%, mp.: 158–159 C.°.

EXAMPLE 11

Preparation of 3-chloro-1-(p-chloro-phenyl)-1,2-dihydro-as-triazino[6,1-a]isoquinolin-5-ium-2-(1H)-ide 1.5 g (0.004 mole) of 3-chloro-1-(p-chloro-phenyl)-as-triazino[6,1-a]isoquinolinium-perchlorate are hydrogenated in a mixture of 0.34 g (0.0041 mole) of sodium acetate and 30 ml of acetic acid in the presence of 0.05 g of a palladium-charcoal catalyst with an equivalent amount of hydrogen. The catalyst is filtered off and the filtrate is evaporated. The residue is dissolved in 5 ml of acetonitrile and 1 ml of 70% perchloric acid is added. The precipitated product is filtered off and dissolved in ethanol. The pH of the solution is adjusted to 9 by adding a 10% sodium hydroxide solution, whereupon 10 ml of water are added. 0.13 g of the crystalline aimed compound are obtained, yield 30%, mp.: 110–113 C.° (from a mixture of dichloromethane and petrolether).

EXAMPLE 12

Preparation of 1-(4-chloro-phenyl)-1-methoxy-as-triazino[6,1-a]isoquinolin-5-ium-2-(1H)-ide To a solution of 4.1 g (0.01 mole) of 1-(4-chloro-phenyl)-1-hydroxy-1,2-dihydro-as-triazino[6,1-a]isoquinolinium-perchlorate and 10 ml of ethanol 16 ml of an aqueous sodium hydroxide solution (1 mole/l) are added, whereupon 1.26 g (0.01 mole) of dimethyl sulfate are added at a temperature below 15 C.°. Thus 2.9 g of the aimed compound are obtained, yield 90%, mp.: 158–159 C.°.

What we claim is:

1. A "Zwitterion" type compound of the Formula I

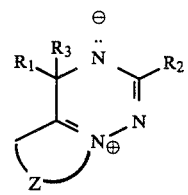

and isomers thereof,
wherein
$R_1$ is $C_1$–$C_{10}$ alkyl, $C_{3-6}$ cycloalkyl of phenyl, naphthyl or phenyl-($C_{1-4}$-alkyl), wherein the aryl ring of the three latter groups may optionally bear one or more halogen, nitro, trifluoromethyl, amino, hydroxy, $C_{1-4}$ alkyl and/or $C_{1-4}$ alkoxy substituents s;
$R_2$ stands for hydrogen, halogen, hydroxy, oxo, $C_{1-4}$ alkyl, $C_{1-4}$ alkoxy or phenyl or naphthyl, wherein the two latter groups may optionally bear one or more halogen, nitro, trifluoromethyl, amino, hydroxy, $C_{1-4}$ alkyl and/or $C_{1-4}$ alkoxy substituents;
$R_3$ represents hydrogen, hydroxy or $C_{1-4}$ alkoxy;
Z is buta-1,3-dienyl or a group of the Formula (a)

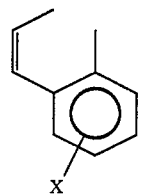

or (b)

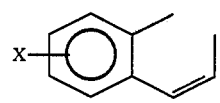

and
X is hydrogen or halogen.

2. A compound according to claim 1, wherein Z is a group of the Formula (b) and X stands for hydrogen.

3. A compound according to claim 1 wherein $R_1$ is phenyl optionally substituted by halogen in position 4.

4. A compound according to claim 1, wherein $R_1$ is 4-chloro-phenyl.

5. 1-(4-Chloro-phenyl)-1-hydroxy-as-triazino[6,1-a]isoquinolin-5-ium-2(1H)-ide.

6. 1-(4-Chloro-phenyl)-as-triazino[6,1-a]isoquinolin-5-ium-B 2-(3H)-ide-3-one.

7. 1-(4-Chloro-phenyl)-1-methoxy-as-triazino[6,1-a]isoquinolin-5-ium-2-(1H)-ide.

8. Pharmaceutical composition having antidepressant and antiarrhythemia effects comprising as active ingredient an effective amount of at least one compound of the Formula I as defined in claim 1, or an isomer thereof, in admixture with suitable inert pharmaceutical solid or liquid carriers.

9. A pharmaceutical composition according to claim 8, comprising as active ingredient
1-(4-chloro-phenyl)-1-hydroxy-as-triazino[6,1-a]isoquinolin-5-ium-2-(1H)-ide;
1-(4-chloro-phenyl)-as-triazino[6,1-a]isoquinolin-5-ium-2-(1H)-ide-3-one;
1-(4-chloro-phenyl)-1-methoxy-as-triazino[6,1-a]isoquinolin-5-ium-2-(1H)-ide.

* * * * *